(12) United States Patent
Yaoi et al.

(10) Patent No.: US 9,171,878 B2
(45) Date of Patent: Oct. 27, 2015

(54) DETECTOR AND DAS, AND X-RAY COMPUTED TOMOGRAPHY APPARATUS

(75) Inventors: Yoshiaki Yaoi, Nasushiobara (JP);
Takayuki Yamazaki, Nasushiobara (JP);
Michito Nakayama, Utsunomiya (JP);
Seiichiro Murai, Yokohama (JP);
Akihiko Taniguchi, Yokohama (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/462,109

(22) Filed: May 2, 2012

(65) Prior Publication Data

US 2013/0101081 A1   Apr. 25, 2013

Related U.S. Application Data

(63) Continuation of application No. PCT/JP2011/074146, filed on Oct. 20, 2011.

(30) Foreign Application Priority Data

Oct. 20, 2010   (JP) .................................. 2010-235312

(51) Int. Cl.
*G01T 1/17*   (2006.01)
*G01T 1/20*   (2006.01)
(Continued)

(52) U.S. Cl.
CPC .......... *H01L 27/14658* (2013.01); *A61B 6/107* (2013.01); *A61B 6/035* (2013.01);
(Continued)

(58) Field of Classification Search
CPC ........ H01L 27/14658–27/14663; A61B 6/107; G01T 1/2928; G01T 1/17; G01T 1/20

USPC ....................................... 378/19; 250/370.09
See application file for complete search history.

(56) References Cited

U.S. PATENT DOCUMENTS 5,848,116 A     12/1998  Sugihara
7,003,076 B2 *   2/2006  Okumura et al. ............ 378/98.8
(Continued)

FOREIGN PATENT DOCUMENTS

CN    101095628 A    1/2008
JP    9-131338       5/1997
(Continued)

OTHER PUBLICATIONS

International Search Report issued Nov. 22, 2011, in PCT/JP2011/074146.

(Continued)

*Primary Examiner* — Glen Kao
*Assistant Examiner* — Dani Fox
(74) *Attorney, Agent, or Firm* — Oblon, McClelland, Maier & Neustadt, L.L.P.

(57) ABSTRACT

According to one embodiment, detector and DAS includes an X-ray detector, a board, a DAS, and a plurality of X-ray shielding plates. The X-ray detector detects X-rays and generates an electrical signal corresponding to the detected X-rays. The board is coupled to the X-ray detector and includes a wiring pattern to extract the electrical signal from the X-ray detector. The DAS is coupled to the board and included an electronic part to perform signal processing for the electrical signal. The X-ray shielding plates are provided for the board to prevent the electronic part from being exposed to X-rays transmitted through the X-ray detector. A portion of the wiring pattern is placed between the X-ray shielding plates.

8 Claims, 8 Drawing Sheets

(51) Int. Cl.
  *H01L 27/146* (2006.01)
  *G21F 3/00* (2006.01)
  *A61B 6/10* (2006.01)
  *G01T 1/29* (2006.01)
  *H04N 5/32* (2006.01)
  *A61B 6/03* (2006.01)
  *A61B 6/00* (2006.01)

(52) U.S. Cl.
  CPC ................ *A61B 6/4291* (2013.01); *G01T 1/17* (2013.01); *G01T 1/20* (2013.01); *G01T 1/2928* (2013.01); *H01L 27/146* (2013.01); *H04N 5/32* (2013.01)

(56) References Cited

U.S. PATENT DOCUMENTS

| | | | |
|---|---|---|---|
| 7,030,918 B1 * | 4/2006 | Nakashiba | 348/294 |
| 7,139,367 B1 * | 11/2006 | Le | 378/98 |
| 7,606,346 B2 * | 10/2009 | Tkaczyk et al. | 378/19 |
| 7,781,741 B2 * | 8/2010 | Narasimhan et al. | 250/394 |
| 2002/0054659 A1 | 5/2002 | Okumura et al. | |
| 2008/0006773 A1 * | 1/2008 | Rose et al. | 250/336.1 |

FOREIGN PATENT DOCUMENTS

| | | |
|---|---|---|
| JP | 2001-215281 | 8/2001 |
| JP | 2003-66149 | 3/2003 |
| JP | 2004-71638 | 3/2004 |
| JP | 2008-6286 | 1/2008 |
| JP | 2009-189384 | 8/2009 |

OTHER PUBLICATIONS

International Preliminary Report on Patentability and Written Opinion issued May 16, 2013 in Application No. PCT/JP2011/074146.
Chinese Office Action mailed on Dec. 26, 2013 in corresponding Chinese Application No. 201180002646.8. (with English translation).

\* cited by examiner

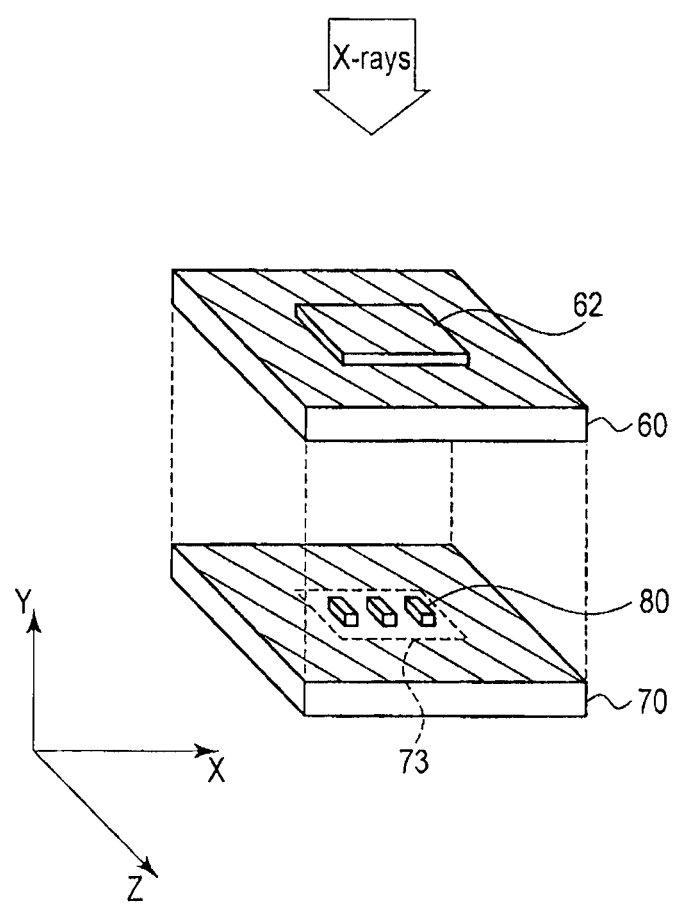
F I G. 4

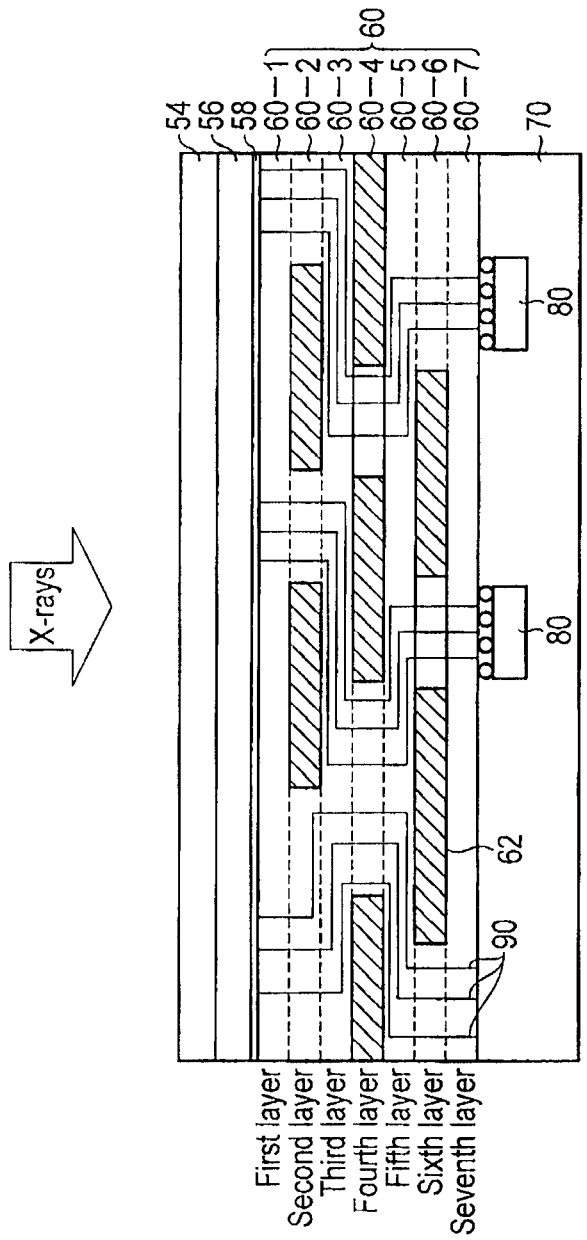
F I G. 6

DETECTOR AND DAS, AND X-RAY COMPUTED TOMOGRAPHY APPARATUS

CROSS REFERENCE TO RELATED APPLICATIONS

This application is a Continuation Application of PCT Application No. PCT/JP2011/074146, filed Oct. 20, 2011 and based upon and claiming the benefit of priority from prior Japanese Patent Application No. 2010-235312, filed Oct. 20, 2010, the entire contents of all of which are incorporated herein by reference.

FIELD

Embodiments described herein relate generally to a detector and DAS (data acquisition system) and an X-ray computed tomography apparatus.

BACKGROUND

An X-ray detector detects X-rays and converts the detected X-rays into analog electrical signals. The X-ray detector is rotatably supported on a rotating frame, together with an X-ray tube. A DAS (Data Acquisition System) is connected to the X-ray detector via a signal cable or the like. The DAS includes electronic parts such as a C-amp chip and an A/D conversion chip. Long-term exposure to radiation such as X-rays will destroy electronic parts. The DAS is therefore placed at a position inside a gantry at which it is not exposed to X-rays.

It is an object to provide a detector and DAS incorporating an X-ray detector and a DAS while preventing the DAS from breaking down due to X-rays, and an X-ray computed tomography apparatus including the detector and DAS.

BRIEF DESCRIPTION OF THE DRAWINGS

FIG. 4 is a perspective view showing a board in FIG. 2 and a DAS in a separate state.

FIG. 6 is a view showing an example of the detector and DAS including a board having a multilayer structure according to this embodiment.

DETAILED DESCRIPTION

In general, according to one embodiment, a detector and DAS includes an X-ray detector, a board, a DAS, and a plurality of X-ray shielding plates. The X-ray detector detects X-rays and generates an electrical signal corresponding to the detected X-rays. The board is coupled to the X-ray detector and includes a wiring pattern to extract the electrical signal from the X-ray detector. The DAS is coupled to the board and included an electronic part to perform signal processing for the electrical signal. The X-ray shielding plates are provided for the board to prevent the electronic part from being exposed to X-rays transmitted through the X-ray detector. A portion of the wiring pattern is placed between the X-ray shielding plates.

A detector and DAS, and X-ray computed tomography apparatus according to an embodiment will be described below with reference to the accompanying drawings.

Figure 1:
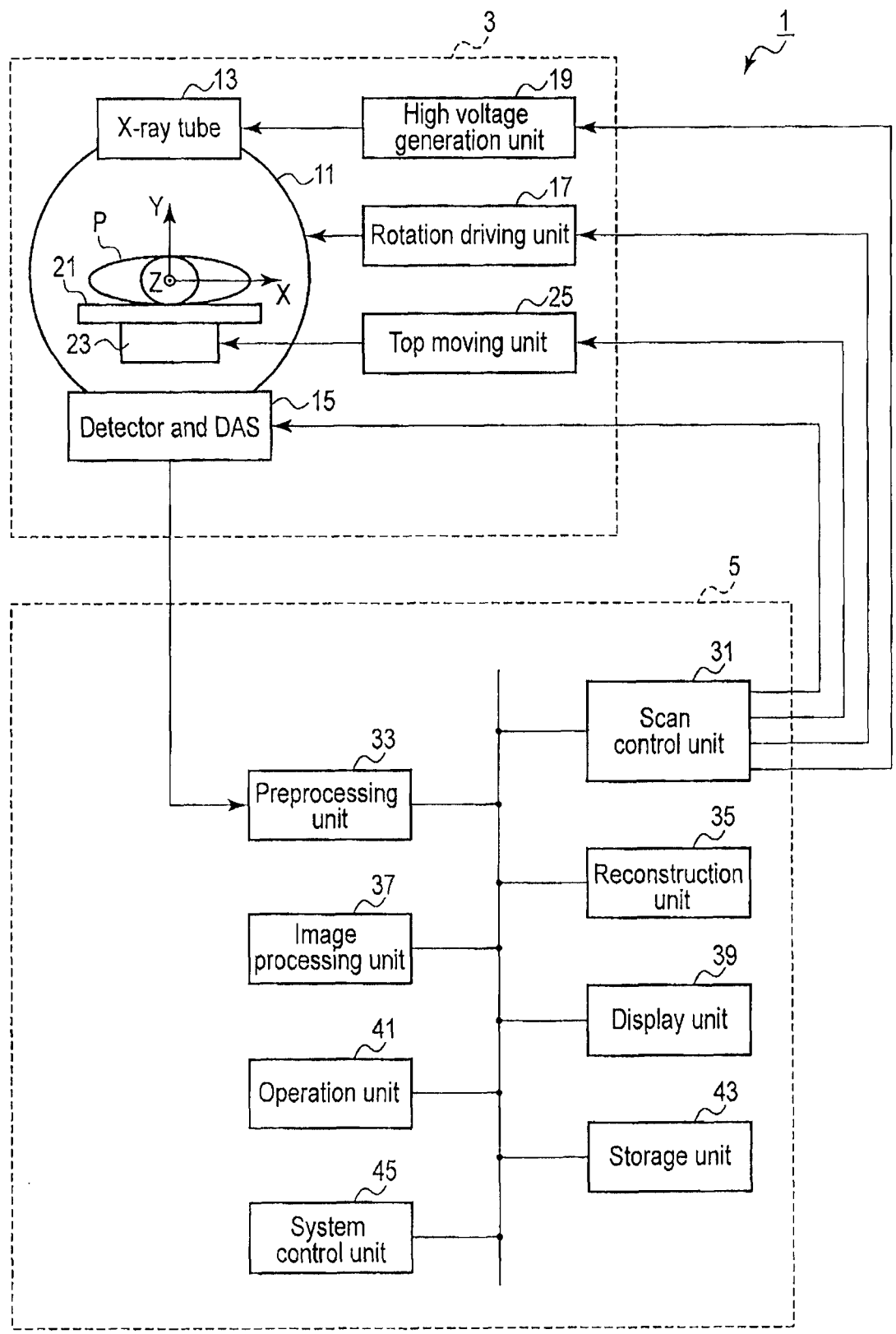
FIG. 1 is a view showing the arrangement of an X-ray computed tomography apparatus according to an embodiment.

FIG. 1 is a view showing the arrangement of an X-ray computed tomography apparatus 1 according to this embodiment. As shown in FIG. 1, the X-ray computed tomography apparatus 1 includes a gantry 3 and a console 5.

The gantry 3 includes an annular or disk-like rotating frame 11. The rotating frame 11 supports an X-ray tube 13 and a detector and DAS 15 so as to allow them to rotate around a subject P. The detector and DAS 15 faces the X-ray tube 13 through an imaging area. The rotating frame 11 is electrically connected to a rotation driving unit 17. The rotation driving unit 17 rotates the rotating frame 11 about its rotation axis so as to rotate the X-ray tube 13 and the detector and DAS 15 around the subject P under the control of a scan control unit 31 in the console 5.

Note that the Z-axis is defined as the rotation axis of the rotating frame 11. The Y-axis is defined as an axis connecting the X-ray focus of the X-ray tube 13 and the center of the X-ray detection surface of the detector and DAS 15. The Y-axis is perpendicular to the Z-axis. The X-axis is defined as an axis perpendicular to the Y- and Z-axes. In this manner, the XYZ orthogonal coordinate system forms a rotating coordinate system which rotates with the rotation of the X-ray tube 13.

The X-ray tube 13 is electrically connected to a high voltage generation unit 19 via a slip ring mechanism (not shown) or the like. The X-ray tube 13 generates X-rays upon reception of a high voltage from the high voltage generation unit 19. The high voltage generation unit 19 applies a high voltage to the X-ray tube 13 under the control of the scan control unit 31.

The detector and DAS 15 implements an integral structure constituted by an X-ray detector 50 and a DAS 70 (data acquisition system) which will be described later. The detector and DAS 15 is electrically connected to the scan control unit 31 via a slip ring mechanism (not shown) or the like. The detector and DAS 15 detects the X-rays generated by the X-ray tube 13 and transmitted through the subject P. The detector and DAS 15 generates digital data corresponding to the detected X-rays under the control of the scan control unit 31. The generated data is supplied to a preprocessing unit 33 of the console 5 via a slip ring mechanism (not shown) or a noncontact data transmission unit (not shown). The structure of the detector and DAS 15 will be described later.

The subject P is placed on a top 21. The top 21 is supported by a top support mechanism 23 so as to be movable along the Z-axis. Typically, the top support mechanism 23 supports the top 21 so as to make the long axis of the top 21 parallel to the Z-axis. The top support mechanism 23 is electrically connected to a top moving unit 25. The top moving unit 25 drives the top support mechanism 23 under the control of the scan control unit 31 to move the top 21 along the Z-axis.

The console 5 includes the scan control unit 31, the preprocessing unit 33, a reconstruction unit 35, an image processing unit 37, a display unit 39, an operation unit 41, a storage unit 43, and a system control unit 45.

The scan control unit 31 controls the detector and DAS 15, the rotation driving unit 17, the high voltage generation unit 19, and the top moving unit 25 to execute a CT scan. The preprocessing unit 33 performs preprocessing such as such as logarithmic transformation and sensitivity correction for the data supplied from the detector and DAS 15. The preprocessed data is called raw data. The reconstruction unit 35 reconstructs image data associated with the subject based on the raw data. The image processing unit 37 performs various kinds of image processing for the image data. The display unit 39 displays the image data generated by the reconstruction unit 35 and the image data processed by the image processing unit 37 on the display. The operation unit 41 accepts various kinds of commands and information inputs from the operator with an input device. The storage unit 43 stores raw data and image data. The storage unit 43 stores control programs for the X-ray CT apparatus. The system control unit 45 reads out control programs stored in the storage unit 43 and expands them in the memory, thereby controlling the respective units in accordance with the expanded control programs.

The structure of the detector and DAS 15 will be described next. The detector and DAS 15 is constituted by a plurality of detector and DAS modules. For example, the detector and DAS modules are arranged two-dimensionally.

Figure 2:
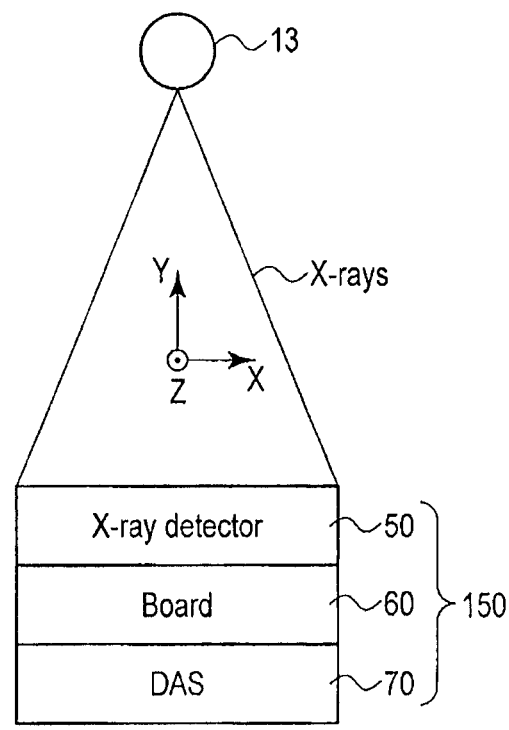
FIG. 2 is a view schematically showing the structure of a detector and DAS module included in a detector and DAS in FIG. 1.

FIG. 2 is a view schematically showing the structure of a detector and DAS module 150. As shown in FIG. 2, the detector and DAS module 150 includes the X-ray detector 50, a board 60, and the DAS 70 which are mechanically connected in the order named from the X-ray tube 13 side.

The X-ray detector 50 detects the X-rays generated from the X-ray tube 13 and transmitted through the subject P, and generates an analog current signal corresponding to the detected X-ray intensity. The X-ray detector 50 includes a plurality of X-ray detection elements arrayed one-dimensionally or two-dimensionally. For example, 1,000 X-ray detection elements are arrayed along an arc centered on the Z-axis. The array direction of these X-ray detection elements is called the channel direction. The Z-axis direction is called the slice direction or row direction. If, for example, the X-ray detector 50 includes 320 rows of X-ray detection elements as a specification, the detector includes 1000×320 X-ray detection elements. In addition, as described above, the detector and DAS is formed by arraying (tiling) a plurality of detector and DAS modules along the channel direction and the slice direction, as described above.

Figure 3:
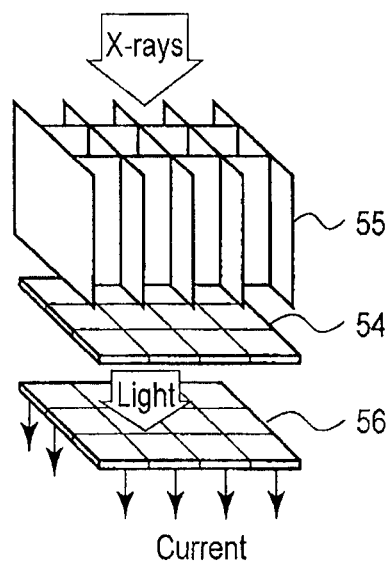
FIG. 3 is an exploded perspective view schematically showing the internal structure of an X-ray detection element included in an X-ray detector in FIG. 2.

FIG. 3 is an exploded perspective view schematically showing the internal structure of an X-ray detection element. As shown in FIG. 3, an X-ray detection element includes a plurality of scintillators 54. The scintillators 54 generate light upon reception of X-rays. The upper surfaces (the surfaces on the X-ray tube side) of the scintillators 54 are provided with a plurality of collimators 55 for removing scattered radiation. A plurality of photodiodes 56 are connected to the lower surfaces of the scintillators 54. The photodiodes 56 convert light generated by the scintillators 54 into current signals. As the photodiodes 56, photodiodes with any existing structures can be used. For example, it is possible to use front-illuminated photodiodes or back-illuminated photodiodes as the photodiodes 56.

FIG. 4 is a perspective view showing the board 60 and the DAS 70 in a separate state. As the board 60, for example, a printed wiring board is used. The board 60 is integrated with the DAS 70. The board 60 exchanges signals with the X-ray detector 50. The DAS 70 includes a plurality of electronic parts 80. The electronic parts 80 are electrically connected to the board 60. The electronic parts 80 may be mounted on the DAS 70 or the board 60 (for example, on the lower surface of the board 60). The electronic parts 80 perform signal processing for electrical signals from the X-ray detector 50. It is possible to use, as the electronic parts 80, electronic parts which can be mounted on an existing DAS, e.g., a C-amp chip for amplifying current signals from the X-ray detector 50 and an A/D conversion chip for converting analog signals into digital signals. The electronic parts 80 have relatively low resistance to X-rays and hence break down when being exposed to X-rays for a long period of time.

On the other hand, the upper surface of the board 60 (surface on the X-ray tube side) is coupled to the lower surface of the X-ray detector 50 (located on the DAS side) so as to be electrically connected to the X-ray detector 50. In this manner, the board 60 is configured to electrically connect the X-ray detector 50 to the electronic parts 80.

An X-ray shielding plate (shield) 62 is provided on a local portion of the board 60. The X-ray shielding plate 62 may be provided on any of the upper surface, lower surface, and inside of the board 60. For example, the X-ray shielding plate 62 is attached to the upper surface of the board 60. The X-ray shielding plate 62 is formed from a heavy metal such as lead, tungsten, or molybdenum. The X-ray shielding plate 62 may be formed from a metal which is a material for wirings, e.g., aluminum. The X-ray shielding plate 62 is provided at a position to shield against X-rays generated from the X-ray tube 13 and transmitted through the X-ray detector 50 so as to prevent the electronic parts 80 from being exposed to X-rays. A wiring pattern is formed inside the board 60 to electrically connect the upper surface of the board 60 (the coupling surface between the board 60 and the X-ray detector 50) to the lower surface (the coupling surface between the board 60 and the DAS 70), thereby electrically connecting the X-ray detector 50 to the electronic parts 80. A wiring pattern is provided for each module of the X-ray detector 50 to allow to extract electrical signals from the X-ray detector 50 to the electronic parts 80. More specifically, wiring patterns are provided on the upper and lower surfaces of the board 60 so as to electrically connect the X-ray detector 50 to the electronic parts 80. A wiring pattern can be formed from a known metal. A wiring pattern may be formed from the same metal as that of the X-ray shielding plate 62 or a metal different from it.

The X-ray shielding plate 62 and the wiring pattern are formed by, for example, etching or photolithography. In this case, a thin metal film such as an aluminum film is attached to the surface of the board 60, and part of the thin metal film is processed into a wiring pattern by photolithography. The remaining thin metal film portion which is not processed into a wiring pattern is used for the X-ray shielding plate 62. The upper and lower surfaces of the board 60 are coated with thin films for the protection and insulation of the board 60. In this embodiment, for example, the X-ray shielding plate 62 and the wiring pattern are formed on the surface of the board 60, and the surface of the board 60 is coated with a thin film so as to cover the X-ray shielding plate 62 and the wiring pattern. In this manner, the X-ray shielding plate 62 and the wiring pattern are provided inside the board 60. In addition, a through hole is formed to extend through the upper and lower surfaces of the board 60. The through hole is provided with a wiring pattern for electrically connecting the wiring pattern provided on the upper surface of the board 60 to the wiring pattern provided on the lower surface.

In this manner, a wiring pattern is formed only on a portion inside the board 60 except for a portion on which the X-ray shielding plate 62 is not provided. Conversely, entirely covering the board 60 with the X-ray shielding plate 62 will make it impossible to form any wiring pattern inside the board 60. Under the circumstances, the X-ray shielding plate 62 is provided on a local portion of the board 60.

The installation position and size of the X-ray shielding plate 62 are designed in accordance with the range on the DAS 70 which is occupied by the electronic parts 80. In this case, the range on the upper surface of the DAS 70 in which the upper surface is not exposed to X-rays because the X-ray shielding plate 62 shields against X-rays will be referred to as a protective range 73. In this case, the installation position and size of the X-ray shielding plate 62 are designed to make the protective range 73 include the installation range of the electronic parts 80. From the viewpoint of the weight saving of the detector and DAS 15, the smaller the X-ray shielding plate 62, the better. It is therefore preferable to design the installation position and size of the X-ray shielding plate 62 so as to almost match the protective range 73 with the installation range of the electronic parts 80.

Note that if the number of X-ray shielding plates 62 to be provided on the board 60 may be one or more if the electronic parts 80 are not exposed to X-rays. According to the above description, the X-ray shielding plate 62 is provided inside the board 60. However, this embodiment is not limited to this. For example, the X-ray shielding plate 62 may be provided on the outer surface of the board 60. That is, the X-ray shielding plate 62 may be provided outside the thin film for protecting and insulating the board 60.

With this structure, the DAS 70 reads out current signals from the X-ray detector 50 for each channel under the control of the scan control unit 31. The DAS 70 generates raw data as digital signals by amplifying readout current signals and converting the amplified current signals into digital signals.

The board 60 in the above arrangement is a single layer. However, the board 60 according to this embodiment is not limited to only a single layer, and may have a multilayer structure. The detector and DAS 15 including the board 60 having a multiplayer structure will be described below.

Figure 5:
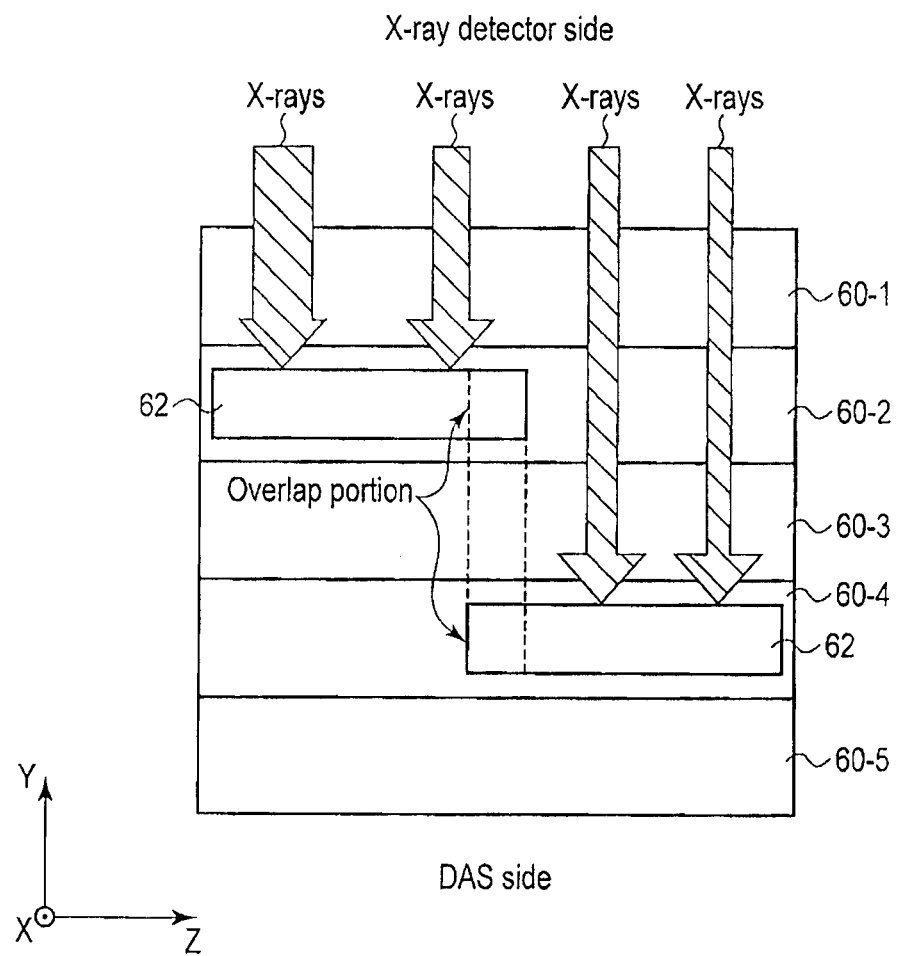
FIG. 5 is a view showing an example of a board having a multilayer structure according to this embodiment.

FIG. 5 is a view showing an example of the structure of the board 60 having a multilayer structure according to this embodiment. Note that the board 60 in FIG. 5 has a YZ section. As shown in FIG. 5, the board 60 has a five-layer structure with five sub-boards (printed wiring boards) 60-n being stacked on each other along the Y-axis. The sub-boards 60-n of the five layers will be sequentially referred to as a sub-board 60-1 of the first layer, a sub-board 60-2 of the second layer, a sub-board 60-3 of the third layer, a sub-board 60-4 of the fourth layer, and a sub-board 60-5 of the fifth layer from the X-ray detector side. The five sub-boards 60 constitute a board unit for electrically connecting the X-ray detector 50 to the DAS 70. Wiring patterns are formed on the upper surface, inside, and lower surface of each sub-board 60 to electrically connect the upper surface of the sub-board 60-1 of the first layer to the lower surface of the sub-board 60-5 of the fifth layer via the sub-boards 60-n.

As shown in FIG. 5, the X-ray shielding plates 62 are provided on the sub-boards 60-n in a staggered pattern (offset pattern) so as to prevent X-rays transmitted through the X-ray detector 50 from being transmitted through the DAS 70. The Y-axis coincides with the central axis direction of each sub-board 60-n. In other words, the X-ray shielding plates 62 are provided in the sub-boards 60-n such that the protective range defined by the X-ray shielding plates 62 includes the installation range of electronic parts on the DAS. Since it is necessary to form a wiring pattern on at least a portion of each sub-board 60-n, the area of each X-ray shielding plate 62 which is associated with an X-Z plane is preferably designed to be smaller than the area of each sub-board 60-n which is associated with an X-Z plane. Arranging the X-ray shielding plates 62, each having a small area, in a staggered pattern allows to electrically connect the X-ray detector 50 to the DAS 70 and can protect the electronic parts 80 from X-rays. In order to reliably shield against X-rays, it is preferable to arrange the X-ray shielding plates 62 so as to make portions of the respective protective ranges defined by the X-ray shielding plates 62 overlap each other when viewed from the incident direction of X-rays.

Typically, the lower surface of the sub-board 60-n of the lowermost layer (the fifth layer in the case shown in FIG. 5) is used for electrical connection to the DAS 70. It is therefore preferable not to provide the X-ray shielding plate 62 on the lower surface of the sub-board 60-n of the lowermost layer. According to the above description, the board 60 has the five-layer structure. However, this embodiment is not limited to this. For example, two, three, four, or six or more sub-boards may be stacked on each other. That is, the board 60 may be formed from a multilayer wiring board constituted by two or more sub-boards. The X-ray shielding plates 62 are provided for the sub-boards 60-n in, for example, a staggered pattern along the central axis of the board 60.

FIG. 6 is a view schematically showing an example of the structure of the detector and DAS 15 including the board 60 having the multiplayer structure. FIG. 6 shows a Y-Z section of the detector and DAS 15. As shown in FIG. 6, the board 60 is coupled to the lower surfaces of the photodiodes 56 via a plurality of terminals 58 (BGA (ball grid array)).

The board 60 in FIG. 6 has a seven-layer structure constituted by seven sub-boards 60-n. In this case, the sub-boards 60-n of the seven layers will be sequentially referred to as a sub-board 60-1 of the first layer, a sub-board 60-2 of the second layer, a sub-board 60-3 of the third layer, a sub-board 60-4 of the fourth layer, a sub-board 60-5 of the fifth layer, a sub-board 60-6 of the sixth layer, and a sub-board 60-7 of the seventh layer from the X-ray detector side. The seven sub-boards 60-n constitute a board unit for electrically connecting the X-ray detector 50 to the DAS 70. The electronic parts 80 are electrically connected to the lower surface of the sub-board 60-7 of the lowermost layer.

The X-ray shielding plates 62 are provided on local portions of the sub-boards 60-n. The X-ray shielding plate 62 may be provided for any of the upper surface, lower surface, and inside of the sub-board 60-n. For example, the X-ray shielding plate 62 is provided on the upper surface of the sub-board 60-n. The X-ray shielding plate 62 is provided to prevent the electronic parts 80 from being exposed to X-rays. For this purpose, the X-ray shielding plates 62 are provided at proper positions on the sub-boards 60-n so as to shield against the X-rays generated by the X-ray tube 13 and transmitted through the X-ray detector 50.

Wiring patterns 90 are provided on the sub-boards 60-n so as to detour the X-ray shielding plates 62. In addition, the wiring patterns 90 are provided on the respective sub-boards 60-n so as to electrically connect the upper surface of the sub-board 60-1 of the first layer to the lower surface of the sub-board 60-7 of the seventh layer. Portions of the wiring patterns 90 are provided between the X-ray shielding plates 62 so as not to physically contact the X-ray shielding plates 62. This can prevent the X-ray shielding plates 62 from being electrically connected to the wiring patterns 90. Note that portions of the wiring patterns 90 are provided between the two X-ray shielding plates 62 within the single sub-board 60-n or provided between the two X-ray shielding plates 62 across the different sub-boards (layers) 60-n. Portions of the wiring patterns 90 mean portions of all wiring paths which connect the upper surface of the sub-board 60-1 of the uppermost layer to the lower surface of the sub-board 60-7 of the lowermost layer.

More specifically, the wiring patterns 90 are provided on the upper and lower surfaces of the respective sub-boards 60-n. In addition, a wiring pattern is formed inside each sub-board 60-n to electrically connect the upper and lower surfaces of each sub-board 60-n. As a result, the X-ray detector 50 is electrically connected to the electronic parts 80. The wiring pattern 90 is provided for each module of the X-ray detector 50 to allow to extract electrical signals from the X-ray detector 50 to the electronic parts 80. The wiring patterns 90 can be formed from a known metal. The wiring patterns 90 may be formed from the same metal as that of the X-ray shielding plates 62 or a metal different from that of the X-ray shielding plates 62.

The X-ray shielding plates 62 and the wiring patterns 90 are formed by, for example, photolithography. In this case, a thin metal film such as an aluminum film is attached to the surface of the sub-board 60-n, and part of the thin metal film is processed into the wiring pattern 90 by photolithography. The remaining thin metal film portion which is not processed into the wiring pattern 90 is used for the X-ray shielding plate 62. The upper and lower surfaces of each sub-board 60-n are coated with thin films for the protection and insulation of the sub-board 60-n. In this embodiment, for example, the X-ray shielding plate 62 and the wiring pattern 90 are exclusively formed on a portion of the surface of the sub-board 60-n, and the surface of the sub-board 60-n is coated with a thin film so as to cover both the X-ray shielding plate 62 and the wiring pattern. In this manner, the X-ray shielding plate 62 and the wiring pattern 90 are provided inside the sub-board 60-n. In addition, a through hole is formed to extend through the upper and lower surfaces of each sub-board 60-n. The through hole is provided with the wiring pattern 90 for electrically connecting the wiring pattern 90 provided on the upper surface of the sub-board 60-n to the wiring pattern provided on the lower surface.

As shown in FIG. 6, the X-ray shielding plates 62 are provided inside the sub-boards 60-n in a staggered pattern (offset pattern) so as to prevent the X-rays transmitted through the X-ray detector 50 from being transmitted through the DAS 70. For example, to facilitate conduction between the X-ray detector 50 and the electronic parts 80, the X-ray shielding plates 62 are alternately provided for the sub-boards 60-n. For example, the X-ray shielding plates 62 are provided for the sub-board 60-2 of the second layer, the sub-board 60-4 of the fourth layer, and the sub-board 60-6 of the sixth layer. The X-ray shielding plates 62 are not provided for the sub-board 60-1 of the first layer, the sub-board 60-3 of the third layer, the sub-board 60-5 of the fifth layer, and the sub-board 60-7 of the seventh layer. The X-ray shielding plates 62 are arranged inside the board 60 in a staggered pattern so as to prevent the electronic parts 80 from being exposed to X-rays. In addition, to reliably shield against X-rays, the X-ray shielding plates 62 are provided such that portions of the X-ray shielding plates 62 arranged on the different sub-boards 60-n overlap each other when viewed from the incident direction of X-rays.

Figure 7:
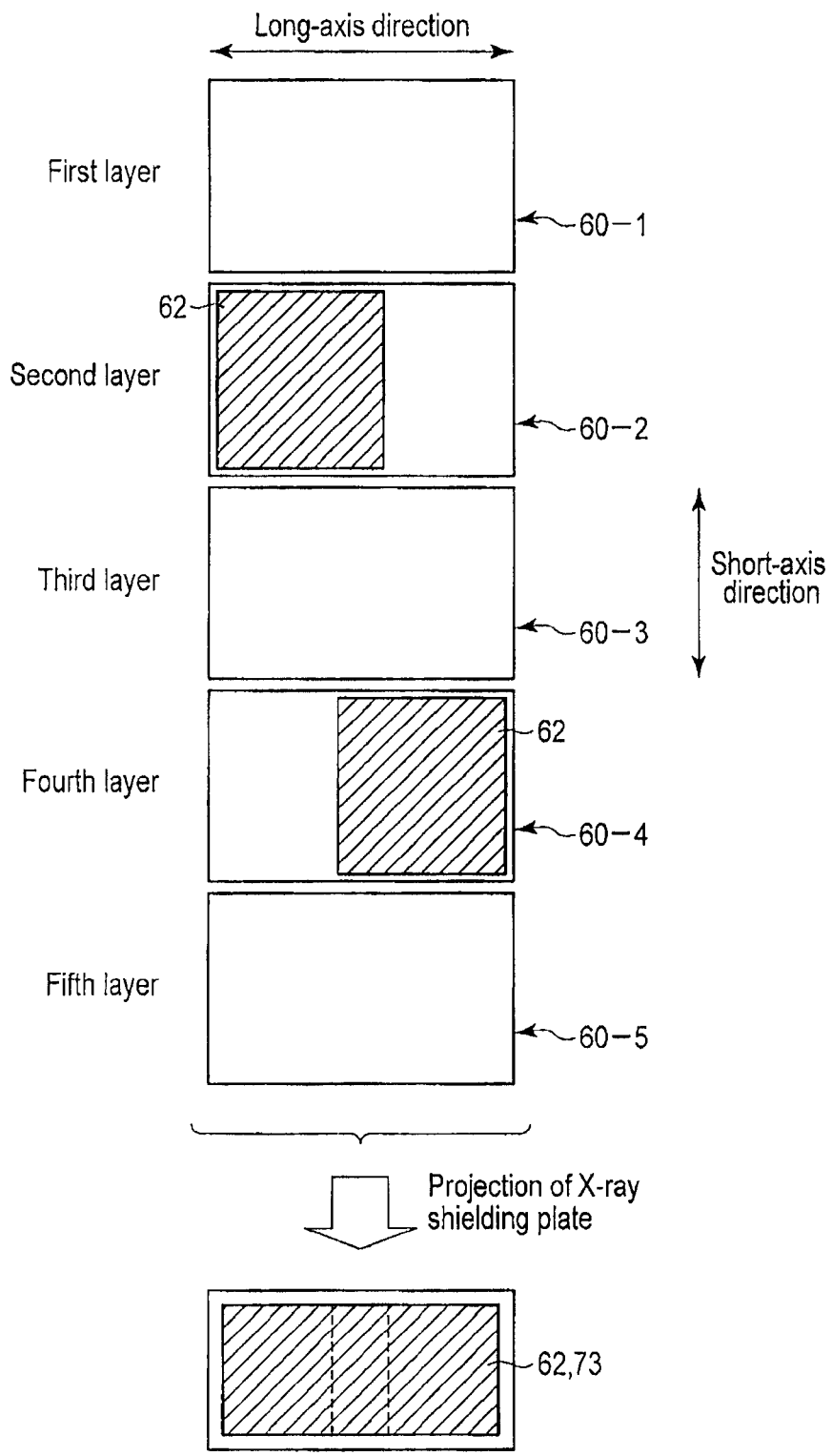
FIG. 7 is a view showing an example of the arrangement of X-ray shielding plates according to this embodiment.
Figure 8:
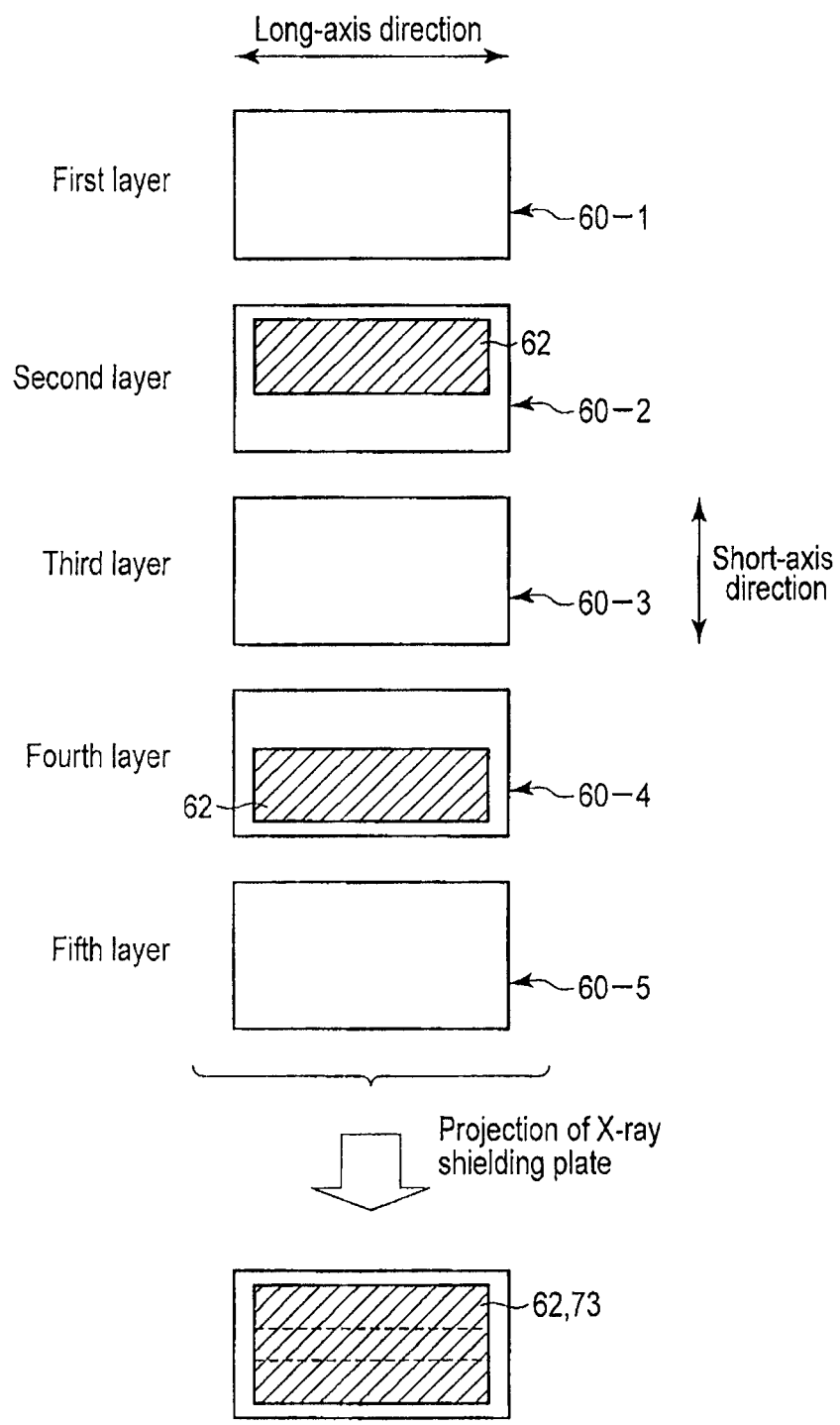
FIG. 8 is a view showing another example of the arrangement of X-ray shielding plates according to this embodiment.
Figure 9:
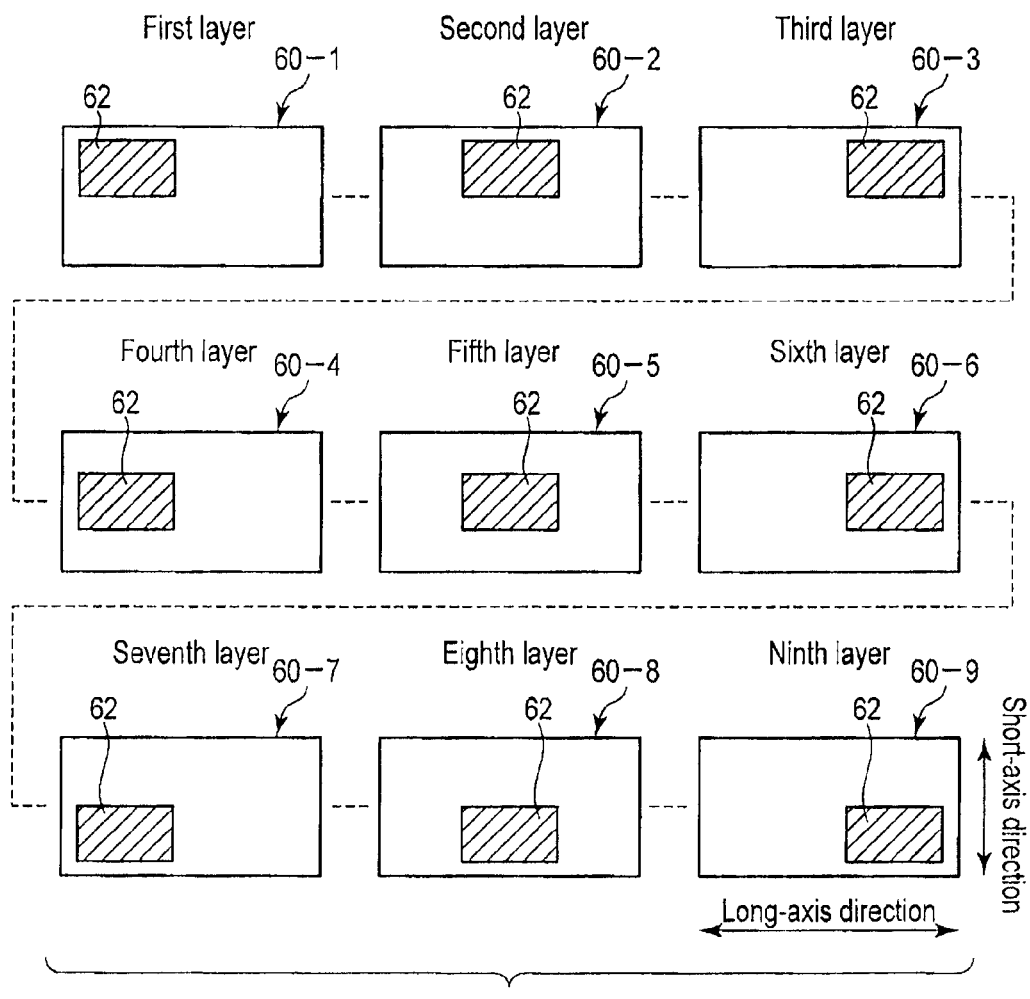
FIG. 9 is a view showing still another example of the arrangement of X-ray shielding plates according to this embodiment.

Variations of the arrangement of the X-ray shielding plates 62 will be described next. FIG. 7 is a view showing an example of the arrangement of the X-ray shielding plates 62. The board 60 in FIG. 7 has a five-layer structure as in FIG. 5 and has five sub-boards 60-n. In the arrangement shown in FIG. 7, the X-ray shielding plates 62 are alternately arranged with respect to the short-axis direction of the sub-boards 60-n. FIG. 8 is a view showing another example of the arrangement of the X-ray shielding plates 62. The board 60 in FIG. 8 has a five-layer structure as in FIG. 5, and has five sub-boards 60-n. In the arrangement shown in FIG. 8, the X-ray shielding plates 62 are alternately arranged with respect to the long-axis direction of the sub-boards 60-n. FIG. 9 is a view showing an example of the arrangement of the X-ray shielding plates 62. The board 60 in FIG. 9 has a nine-layer structure as in FIG. 5, and has nine sub-boards 60-n. In the arrangement shown in FIG. 9, the X-ray shielding plates 62 are arranged at different positions on the respective sub-boards 60-n.

In either of the arrangements shown in FIGS. 7, 8, and 9, the X-ray shielding plates 62 and the arrangement patterns 90 are provided for the board 60 such that the protective range produced by the of X-ray shielding plates 62 covers the installation range of the electronic parts 80, and the upper surface of the sub-board of the uppermost layer is electrically connected to the lower surface of the sub-board of the lowermost layer via the sub-boards 60-n. In other words, since the arrangement patterns 90 are provided between the X-ray shielding plates 62, and for reliable shielding against X-rays, it is preferable to arrange the X-ray shielding plates 62 such that portions of the X-ray shielding plates 62 arranged on the different sub-boards 60-n overlap each other when viewed from the incident direction of X-rays.

In order to reliably protect the electronic parts 80 distributed in a wide range against X-rays, the X-ray shielding plates 62 need to be provided in a wide range on the board 60. In the case of a single-layer structure, therefore, the board 60 is mostly occupied by the X-ray shielding plates 62, resulting in a difficulty in securing zones for the formation of the wiring patterns 90. In the case of a multilayer structure, the X-ray shielding plates 62, each having a small area as compared with the single-layer structure, can be selectively provided for the sub-boards 60-n. As compared with a single-layer structure, therefore, a multiplayer structure facilitates securing zones for the formation of the wiring patterns 90 on the respective sub-boards 60-n. In addition, as compared with a single-layer structure, a multilayer structure allows to arrange many X-ray shielding members on the propagation paths of X-rays to the electronic parts 80 by making portions of the X-ray shielding plates 62 overlap each other. As compared with a single-layer structure, a multilayer structure can attenuate the energy of X-rays propagating toward the electronic parts 80s.

As described above, the X-ray computed tomography apparatus 1 according to this embodiment includes the board 60 provided with the X-ray shielding plates 62 between the X-ray detector 50 and the DAS 70. The X-ray detector 50, the board 60, and the DAS 70 are sequentially connected to each other along the Y-axis. The X-ray shielding plates 62 are arranged to prevent the X-rays generated from the X-ray tube 13 from irradiating the electronic parts 80 on the DAS 70. The board 60 is provided with the wiring patterns 90 for extracting electrical signals from the X-ray detector 50. The wiring patterns 90 are provided between the X-ray shielding plates 62.

With this arrangement, the X-ray computed tomography apparatus 1 implements the detector and DAS 15 incorporating the X-ray detector 50 and the DAS 70 while protecting the DAS 70 against X-rays. Implementing the detector and DAS 15 allows to manufacture the compact gantry 3 as compared with the prior art in which the X-ray detector 50 and the DAS 70 are separate from each other. The conventional structure in which the X-ray detector 50 and the DAS 70 are connected to each other via a signal cable cannot avoid the generation of noise when a current signal passes through the signal cable. In contrast to this, since the detector and DAS 15 according to this embodiment uses no signal cable, it is possible to reduce the generation of noise in the path from the X-ray detector 50 to the DAS 70 as compared with the conventional structure. In addition, since this embodiment requires no signal cable, it is possible to achieve a reduction in cost corresponding to the signal cable.

In addition, as described above, the detector and DAS 15 is constituted by the detector and DAS modules 150, and the function and structure of the detector and DAS 15 are modularized. It is possible to arrange (tile) the detector and DAS module 150 in the slice direction or the channel direction. When the X-ray detector 50 and the DAS 70 are connected to each other along the slice direction or the channel direction, it is structurally impossible to implement tiling. In this embodiment, since the X-ray detector 50 and the DAS 70 are connected along the Y-axis, it is possible to tile the detector and DAS modules 150. This makes it easy to expand the X-ray detection range in the slice direction or the channel direction. In addition, since the detector and DAS 15 is segmented into a plurality of detector and DAS modules 150, even if one detector and DAS module 150 breaks down, it is possible to replace only the failed detector and DAS module 150 instead of replacing the entire detector and DAS 15. The X-ray computed tomography apparatus 1 according to this embodiment, more specifically, the detector and DAS 15 facilitates repair and has an economical advantage.

As has been described above, the X-ray computed tomography apparatus 1 and detector and DAS 15 according to this embodiment can integrate the X-ray detector 50 and the DAS 70 while preventing the DAS 70 from breaking down due to X-rays.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A detector and DAS comprising:
an X-ray detector configured to detect X-rays and generate an electrical signal corresponding to the detected X-rays;
a board coupled to a back surface the X-ray detector and including a wiring pattern to extract the electrical signal from the X-ray detector;
a data acquisition circuit coupled to a back surface the board and including an electronic part to perform signal processing for the electrical signal; and
a plurality of X-ray shielding plates provided for the board to prevent the electronic part from being exposed to X-rays transmitted through the X-ray detector,
wherein the wiring pattern connects the X-ray detector and the data acquisition circuit and detours around the X-ray shielding plates,
wherein a portion of the wiring pattern is placed between the X-ray shielding plates, and
wherein a portion of the wiring pattern is placed between the X-ray shielding plates, and
wherein the plurality of X-ray shielding plates are provided to overlap each other when viewed from an incident direction of the X-rays.

2. The detector and DAS of claim 1, wherein the X-ray shielding plates are arranged between the electronic part and the X-ray detector so as to cover the electronic part.

3. The detector and DAS of claim 1, wherein the board comprises a plurality of sub-boards, and
the X-ray shielding plates are provided for the sub-boards.

4. The detector and DAS of claim 3, wherein the X-ray shielding plates are provided in a staggered pattern.

5. An X-ray computed tomography apparatus comprising:
an X-ray tube configured to generate X-rays;
a detector and DAS configured to detect X-rays generated from the X-ray tube and transmitted through an subject and generate raw data in accordance with the detected X-rays; and
a support mechanism configured to rotatably support the X-ray tube and the detector and DAS,
wherein the detector and DAS comprises
an X-ray detector configured to detect X-rays and generate an electrical signal corresponding to the detected X-rays,
a board coupled to a back surface of the X-ray detector and including a wiring pattern to extract the electrical signal from the X-ray detector,
a data acquisition circuit coupled to a back surface of the board and including an electronic part to perform signal processing for the electrical signal, and
a plurality of X-ray shielding plates provided for the board to prevent the electronic part from being exposed to X-rays transmitted through the X-ray detector, wherein
the wiring pattern connects the X-ray detector and the data acquisition circuit and detours around the X-ray shielding plates,
a portion of the wiring pattern is placed between the X-ray shielding plates, and
the plurality of X-ray shielding plates are provided to overlap each other when viewed from an incident direction of the X-rays.

6. The X-ray computed tomography apparatus of claim 5, wherein the X-ray shielding plates are arranged between the electronic part and the X-ray detector so as to cover the electronic part.

7. The X-ray computed tomography apparatus of claim 5, wherein the board comprises a plurality of sub-boards, and
the X-ray shielding plates are provided for the sub-boards.

8. The X-ray computed tomography apparatus of claim 7, wherein the X-ray shielding plates are provided in a staggered pattern.

* * * * *